United States Patent
Siejko et al.

(10) Patent No.: US 7,713,213 B2
(45) Date of Patent: May 11, 2010

(54) PHYSIOLOGICAL EVENT DETECTION SYSTEMS AND METHODS

(75) Inventors: Krzysztof Z. Siejko, Maple Grove, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 999 days.

(21) Appl. No.: 11/276,735

(22) Filed: Mar. 13, 2006

(65) Prior Publication Data

US 2007/0213599 A1 Sep. 13, 2007

(51) Int. Cl.
A61B 5/02 (2006.01)
(52) U.S. Cl. ..................................... 600/508
(58) Field of Classification Search .................. 600/508
See application file for complete search history.

(56) References Cited

U.S. PATENT DOCUMENTS

| | | | |
|---|---|---|---|
| 6,527,729 | B1 | 3/2003 | Turcott |
| 6,821,249 | B2 | 11/2004 | Casscells, III et al. |
| 2003/0060851 | A1 | 3/2003 | Kramer et al. |
| 2003/0092975 | A1 | 5/2003 | Casscells, III et al. |
| 2005/0059897 | A1* | 3/2005 | Snell et al. ................... 600/510 |
| 2005/0149136 | A1 | 7/2005 | Siejko et al. |

OTHER PUBLICATIONS

Rohling, H., "Radar CFAR Thresholding in Clutter and Multiple Target Situations", *IEEE Trans. Aerosp. Electron. Syst.*, vol. AES-19, No. 4, (Jul. 1983), 608-621.
Rohling, H., "Some radar topics: waveform design, range CFAR and target recognition", *NATO Advanced Study Institute, Advances in Sensing with Security Applications*, (2005), 1-30.

* cited by examiner

*Primary Examiner*—Mark W Bockelman
*Assistant Examiner*—Eric D. Bertram
(74) *Attorney, Agent, or Firm*—Schwegman, Lundberg & Woessner, P.A.

(57) ABSTRACT

Systems and methods using constant false alarm rate techniques for event detection. One example of an event detection method includes collecting a first distribution of measurements for a first physiological parameter. In another example, the first distribution of measurements includes only non-event measurements. One or more values are determined corresponding to at least a first tail area of the first distribution from at least one measurement of the first physiological parameter toward an end point of the distribution. A threshold is established based on a specified false alarm rate. The one or more values are compared to the threshold. The method includes determining if the measurement is representative of a detected event using the comparison.

29 Claims, 11 Drawing Sheets

PHYSIOLOGICAL EVENT DETECTION SYSTEMS AND METHODS

TECHNICAL FIELD

The technical field includes event detection with biomedical devices and in particular event detection using constant false alarm rate techniques.

BACKGROUND

The body includes a plurality of organs and systems that perform functions necessary for maintaining the health of a person. The circulatory system is one example of a system that includes the heart organ as its centerpiece. Other body systems include the respiratory system, digestive system, endocrine system, nervous system and the like. The organs of these systems provide a variety of physiological parameters useful for observing the normal and abnormal behaviors of the body. Observation of these parameters and recognition of potential normal and abnormal events through observation allows effective diagnosis or treatment of diseases, conditions and the like. The complexity of the various systems of the body provide multiple parameters that, when observed, provide insight regarding the onset of a condition or disease. Measuring each of these parameters and correctly identifying when measurements indicate a condition is difficult. Identifying a condition becomes even more difficult when some measurements indicate the onset or existence of a condition or disease while others do not.

One example of a body system is the circulatory system. The heart is the central organ for the circulatory system and includes an electromechanical system performing two major pumping functions. The left portions of the heart draw oxygenated blood from the lungs and pump it to the organs of the body to provide the organs with oxygen. The right portions of the heart draw deoxygenated blood from the organs and pump it into the lungs where the blood is oxygenated. The pumping functions are accomplished by contractions of the heart. An increase in the body's metabolic need for oxygen is satisfied primarily by a higher frequency of the contractions, i.e., a higher heart rate, along with changes in stroke volume.

Various electrical and mechanical functions of the heart provide a variety of physiological parameters that can indicate the onset of a condition, for instance, heart failure, arrhythmia (fibrillation, tachycardia, bradycardia), ischemia, and the like. These physiological parameters include, for example, heart sounds (e.g., S3 amplitude), DC impedance near the lungs, heart rate, respiration rate, weight, and intracardiac pressure. At least some of these parameters may indicate the onset or change of a condition and thereby provide an alert that therapy or therapy adjustment is needed, such as defibrillation, change in pacing schema and the like. It is difficult, however, to determine when an event is beginning when only some measurements for these parameters indicate the onset of a condition.

In some examples, clinicians set measured parameter thresholds in implantable medical devices, such as pacemakers, defibrillators, cardiac resynchronization devices, and the like. The threshold for each parameter may vary from patient to patient and the clinician typically makes educated guesses to determine each threshold. This process of determining an appropriate threshold is then repeated for each parameter of interest. Configuring the pulse generator can therefore become a tedious, time-consuming exercise that may involve guesswork on the part of the clinician. Moreover, many clinicians adopt a conservative approach geared toward applying therapy even when therapy may not be needed. For example, measured parameter thresholds may be set intentionally low to provide therapy in every instance it may be needed. Therapy is thereby provided when at least one or more of the measurements for a parameter are above the set threshold—even when the measurements for other parameters indicate there is not an event. False positives, non-events that include measurements above at least some thresholds, thereby initiate treatment. In some circumstances, such as defibrillation shock therapy, the user of the implantable medical device receives painful and unnecessary treatment in response to such a false positive. The issues described above, with regard to cardiac therapy, such as setting thresholds, conservative thresholds and the like, extend to other medical devices associated with the other organs and systems of the body.

The present inventors have recognized that event detection systems and methods that address the above issues are needed. That present inventors have also recognized that what is further needed are event detection systems and methods that facilitate rapid and accurate setting of thresholds to apply appropriate therapy in biomedical devices.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

Figure 1:
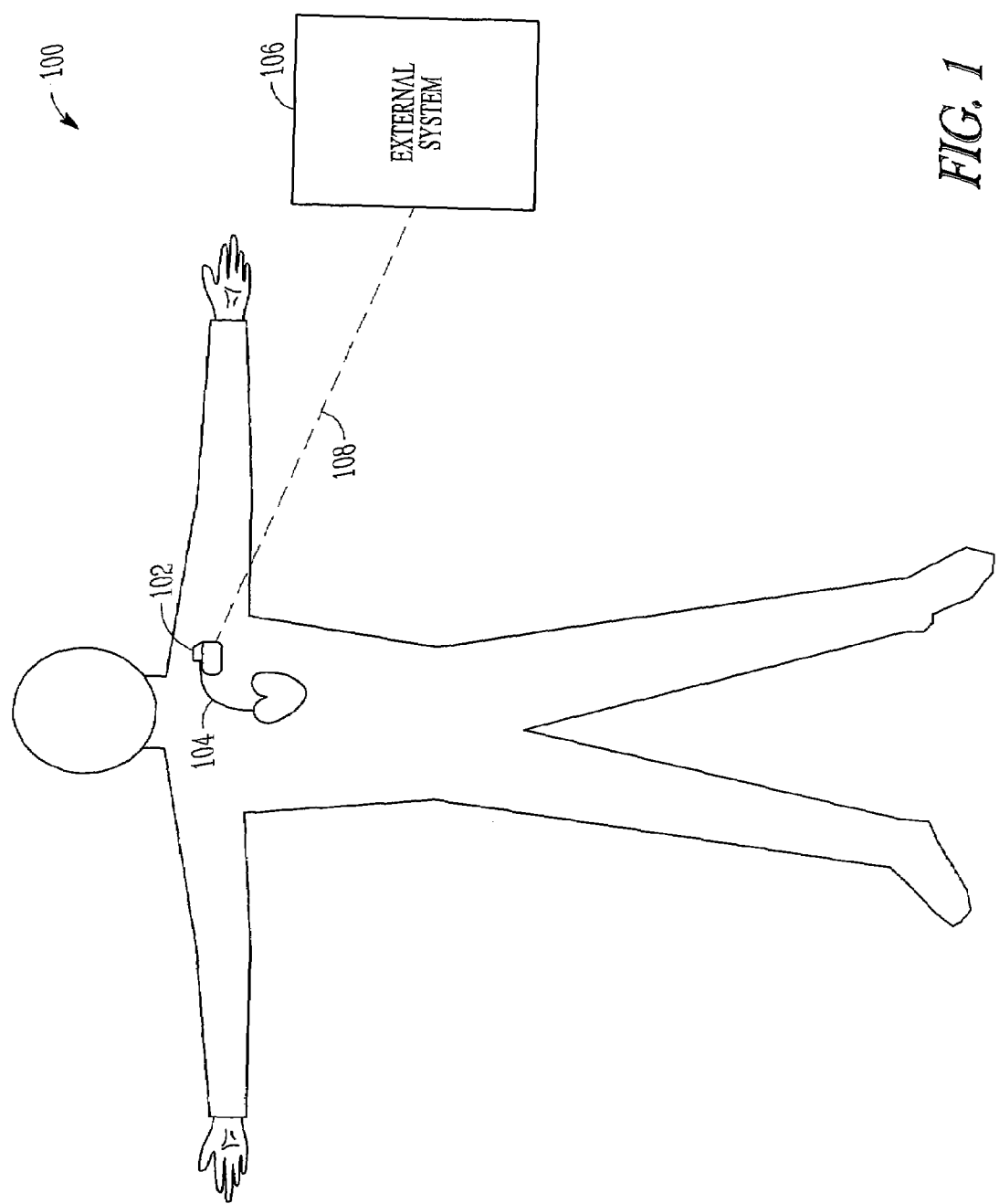
FIG. 1 is a schematic diagram showing one example of a cardiac management system.

FIG. 1 is a schematic diagram showing one example of portions of a cardiac management system 100 including an implantable medical device 102, a lead system 104, an external system 106, and a wireless telemetry link 108. In one example, the implantable medical device includes a cardiac rhythm management device, such as a cardiac pacemaker, defibrillator, combination pacemaker/defibrillator, or the like. In another example, the external system 106 includes a wireless server system, such as the LATITUDE® system, a registered trademark of Cardiac Pacemakers, Inc. of St. Paul, Minn.

In one example, the lead system 104 includes conductors and electrodes adapted to provide electrical stimulation to the tissues of the heart and surrounding area. In another example, the electrodes of the lead system 104 are used to measure one or more physiological parameters associated with the heart, including, but not limited to heart sound amplitude, heart rate, intracardiac pressure and the like. In still another example, the lead system 104 and the implantable medical device 102 cooperate to measure one or more physiological parameters, such as, but not limited to, DC impedance across the lungs, respiration rate of the lungs and the like.

Figure 2:
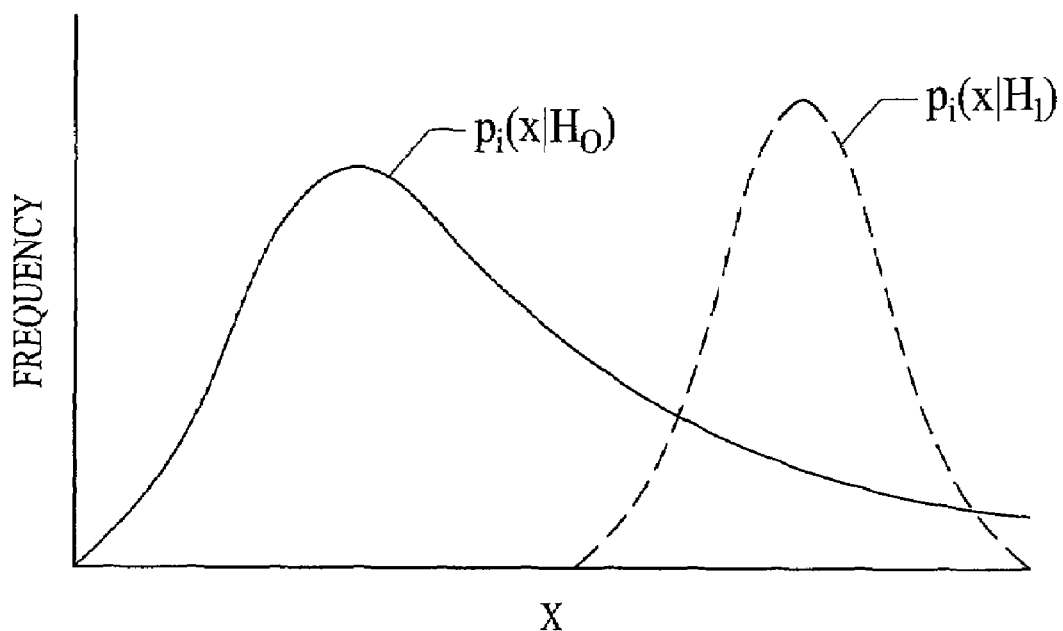
FIG. 2 is a plot showing one example of a probability distribution function for non-event measurements and an estimated probability distribution function for event data.

FIG. 2 shows one example of a probability density function $p_i(x|H_0)$ based upon measurements taken over a period time for a physiological parameter (e.g., heart sound amplitude, heart rate and the like) of a patient. In one example, the function $p_i(x|H_0)$ shows a distribution for non-event (baseline) measurements taken for the physiological parameter. The function $p_i(x|H_0)$ thereby shows a distribution of measurements for a stable patient. These measurements are readily taken during everyday living and statistically characterize the non-event environment of the patient (i.e., no heart failure, arrhythmia, and the like). In other words, $H_0$ is the hypothesis that there are no events of physiological significance, such as heart failure, fibrillation and the like. The probability density function $p_i(x|H_1)$ shown in dashed lines in FIG. 1, illustrates an estimated distribution of measurements for a physiological parameter representative of an "event" condition (e.g., heart failure, arrhythmia and the like). Because event measurements are typically rare, the function $p_i(x|H_1)$ typically only approximates the distribution of event-related measurements. $H_1$ thereby is the hypothesis showing events of significance. In another example, $H_1$ is estimated from a population of past events. As shown in FIG. 2 and further described below, outlier measurements of the physiological parameter that approach the event distribution $p_i(x|H_1)$ are less likely to be a false alarm (i.e., decreased probability of not being indicative of an event), and conversely an increased probability of being indicative of an event (e.g., heart failure, arrhythmia and the like). Conceptually, measurements that are outliers for $p_i(x|H_0)$ more closely resemble event measurements than non-event measurements.

In one example, the probability density function $p_i(x|H_0)$ is generated using a histogram of actual measured values. The actual measured values are used to directly estimate the probability density function. Properties of the measurements (e.g., median and percentile measure) are used to create the probability density function. By contrast, in another example, a particular probability distribution is used, such as a Gaussian distribution or other function that is specified mathematically (e.g., by estimating the mean and standard deviation) or otherwise. In still another example, the probability density function is generated by curve-fitting over histogram data. The measurements used to generate the probability density function $p_i(x|H_0)$ are collected and stored, such as in at least one of the implantable medical device 102 and the external system 106 (FIG. 1). In another option, the probability density function $p_i(x|H_0)$ is generated in at least one of the implantable medical device 102 and the external system 106.

In certain examples, particular measurements are excluded from use in computing the probability density function $p(x_i|H_0)$, such as corrupted measurements, old measurements, event-related measurements—the function $p_i(x|H_0)$ should only include non-event data—and the like. In one example, the probability distribution function is generated with measurements taken during a particular (e.g., moving) window of time. In certain examples, the moving window of time extends a specified interval back from the time of the most recent measurement of the physiological parameter. In certain examples, older measurements outside of the moving window of time are excluded from use in computing the probability distribution function. This allows the probability distribution function to update and follow gradual drifts in the physiological parameter by using the most recent measurements. Older measurements can be stored in the implantable medical device and/or external system, such as for historical use. Additionally, where measurements are determined to indicate an event, as described below, such event-related measurements are flagged and excluded from use in generating the non-event probability distribution function.

In certain examples, measurements that are deemed unreliable or corrupted are not used to compute the non-event probability distribution function. For example, certain physiological parameters are confounded by other effects. For example, heart sounds may be affected by posture. A second sensor (e.g., a posture detector) can be used to detect posture to "qualify" the heart sounds data, such that only heart sounds associated with a particular posture are used to compute a particular probability distribution function—or different probability distribution functions can be computed for various postures. Similarly, certain physiological parameters are affected by sleep state, such that measurements generated during periods of rest, such as sleep, may vary from measurements taken during waking hours. In this example, a sleep detector may be used to qualify the primary physiological parameter according to a particular sleep state. In general, one or more secondary physiological sensors can be used to qualify data from a primary physiological sensor to remove unreliable or corrupted data from use in computing the probability distribution function, which is also useful in a situation in which the primary physiological sensor fails.

Figure 3:
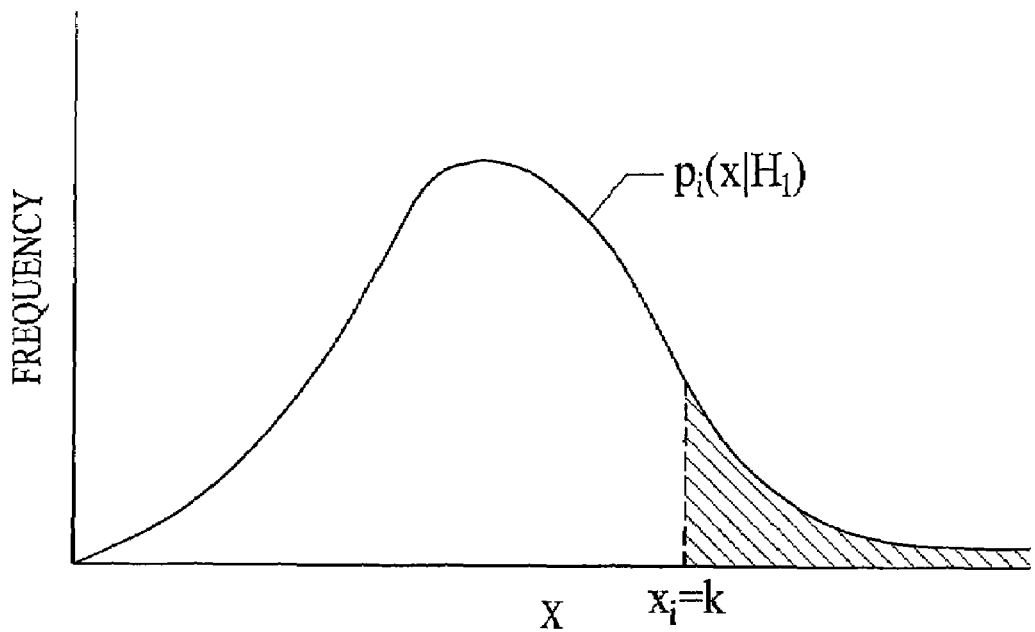
FIG. 3 is a plot showing the example of the non-event probability distribution function with a tail area corresponding to the instantaneous probability of a measurement $x_i$ being a false alarm.

FIG. 3 shows one example of the non-event probability density function $p(x_i|H_0)$. As described above, the function $p_i(x|H_0)$ is typically derived from non-event measurements taken by a sensor of a physiological parameter for the patient. A measurement, such as an instant measurement $x_i=k$ can be plotted along the probability density function $p_i(x|H_0)$ and a confidence is derived by integrating the tail area based on the following equation:

$$C_i = \int_k^\infty p_i(x \mid H_0)dx$$

The confidence $C_i$ is proportional to the instantaneous probability the measurement k is a false alarm (i.e., a non-event measurement). Integration of the probability density function $p_i(x|H_0)$ tail area from the measurement k toward the end of the distribution thereby determines the instantaneous probability that k is a false alarm. A measurement that approaches the end of the distribution has a decreased probability that it indicates a false alarm. It is conversely more probable that such a measurement is indicative of an event, such as the onset of an abnormal condition (e.g., heart failure). The measurement k is typically an existing measurement already recorded by at least one of the implantable medical device 102 and the external system 106.

Figure 4:
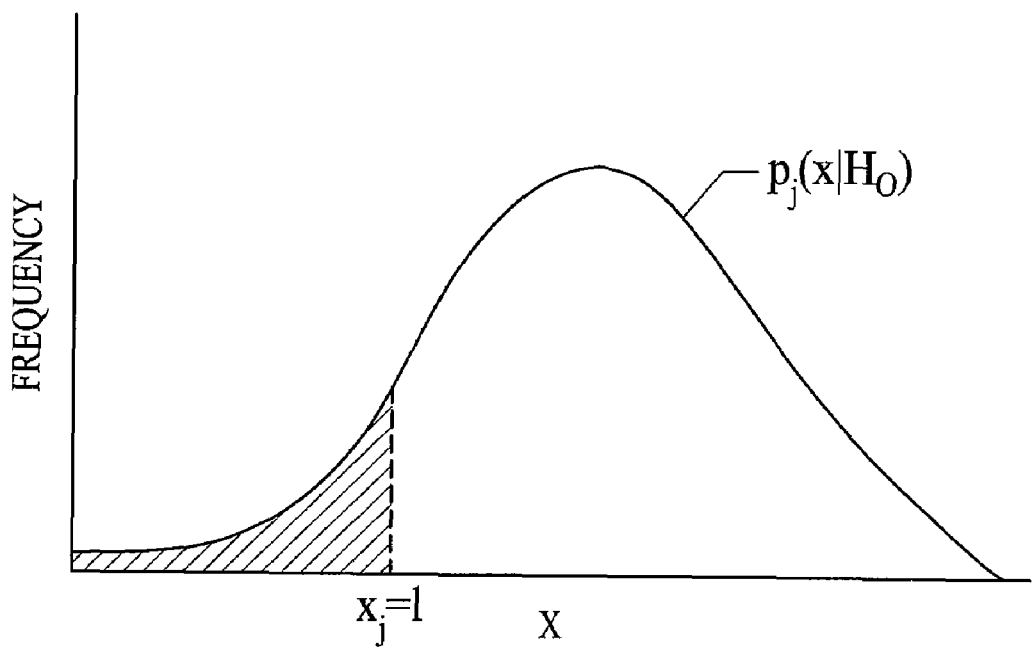
FIG. 4 is a plot showing an example of a negative tailed non-event probability distribution function with a tail area corresponding to the instantaneous probability of a measurement $x_j$ being a false alarm.

FIG. 4 shows another example, in which a function $p_j(x|H_0)$ is represented by a negative-tailed distribution of measurements for a physiological parameter. One example of a physiological parameter having a negative-tailed distribution is near-DC thoracic impedance. Generally, depressed DC thoracic impedance measurements (e.g., intrathoracic total impedance) indicate fluid accumulation, which may be associated with pulmonary edema. Therefore, such depressed DC thoracic impedance measurements represent a decreased probability of false alarm in a pulmonary edema detection scheme. Like the function $p_i(x|H_0)$, function $p_j(x|H_0)$ is typically derived from non-event measurements taken by a sensor of a physiological parameter for the patient. A measurement, such as an instant measurement $x_j=1$ can be plotted along the probability density function $p_j(x|H_0)$ and a confidence is derived by integrating the tail area based on the following equation:

$$C_j = \int_{-\infty}^l p_j(x \mid H_0)dx$$

The confidence $C_j$ is proportional to the instantaneous probability the measurement 1 is a false alarm (i.e., a non-event measurement). Integration of the probability density function $p_j(x|H_0)$ tail area from the measurement 1 toward the left end of the distribution determines the instantaneous probability that 1 is a false alarm. As with the function $p_i(x|H_0)$, a measurement that approaches the end of the distribution, has a decreased instantaneous probability that it indicates a false alarm, and it is conversely more probable that the measurement is indicative of an event, such as the onset of a condition (e.g., heart failure). Optionally, the value corresponding to the "end" of the distribution need not occur +/−infinity, but can instead be approximated using the estimated end of the distribution (e.g., an approximated value approaching a measured end of the distribution, an actual measured value, a value approaching +/−infinity and the like).

In certain examples, the clinician sets a threshold based on a constant specified false alarm rate (FAR) (i.e., constant false alarm rate). For example, the physician can specify that the threshold should be automatically set such that it yields false alarms approximately 5% (0.05) of the time. This specified FAR is independent of any statistical-based analysis of the distribution for a physiological parameter and thereby independent of any influence from the distribution. From the clinician-specified FAR, a threshold can be automatically determined, such as to compare against the values corresponding to the confidences generated with equations, such as those shown for $C_i$ and $C_j$. If the values corresponding to the confidences exceed the FAR-based threshold, then, in certain examples, a therapy is provided in response to the detected physiological event. In one example, the threshold is a value proportional to a specificity desired by the clinician. For instance, in a situation where the patient is susceptible to a condition (e.g., has shown precursor symptoms, has a history of condition and the like) the clinician would likely set a low threshold to ensure that a patient at higher risk of the condition is provided therapy. In another example, where the patient is unlikely to experience the condition (e.g., the patient has a combination pacemaker/defibrillator, but is not expected to experience heart failure) the clinician would set a high threshold to ensure that the low risk patient is only treated if measurements indicate there is a high instantaneous probability of the onset of the condition.

In certain examples, the FAR set by the clinician is converted as shown below to generate a Threshold that is comparable with a similarly transformed confidence (also shown below).

$$\text{Threshold} = -\text{Log}_{10}(FAR)$$

$$Z_i = -\text{Log}_{10}\left[\int_k^\infty p_i(x \mid H_o)dx\right]$$

The Z metric corresponds to the confidence value $C_i$ as described above (i.e., the instantaneous probability of a false alarm for the measurement $x_i=k$). The negative logarithm converts the confidence into a Z-metric value that is comparable with the threshold value generated with a corresponding negative logarithm applied to the FAR. The logarithms provide a means for transforming the FAR and the confidences into comparable values. In other examples, one or more other functions are used to compare the FAR and the confidences including, but not limited to, other logarithms (e.g., natural logarithm) and the like. Additionally, using a logarithm provides visible significance between confidences and the FAR for a clinician to review otherwise similar-appearing values. Once the FAR is converted to the Threshold value and the confidence is converted to the Z metric value, the Threshold and Z metric values are compared. For instance, where the FAR is one false alarm every 365 days, in one example, the corresponding Threshold generated with the above equation is 2.56. If the measurement $x_i=k$ provides an eight percent (0.08) instantaneous probability the measurement is a false alarm (see the $C_i$ equation above) the corresponding Z metric is approximately 1.10. Because the Z metric is not greater than the Threshold, no event would be declared and an alert or therapy would not be provided based on the clinician-set FAR. Conversely, in another example, if the measurement $x_i=k$ provides a 0.1 percent (0.001) instantaneous probability the measurement is a false alarm, the corresponding Z metric is 3 and exceeds the Threshold value of 2.56. In this example, an event is deemed to have occurred, and an alert or therapy is provided based on the clinician-set FAR. In yet another example, a more sensitive FAR is set of 30 false alarms every 365 days, thereby generating a Threshold of approximately 1.09. The eight percent (0.08) instantaneous probability with a corresponding Z metric of 1.10, described above, would exceed the more sensitive Threshold of 1.09 and result in declaring an event to have occurred, which, in turn may result in the generation of an alert, for instance by an alert module, or therapy to the patient.

The Z metric can be used to provide a value corresponding to the instantaneous probability of false alarm for a physiological parameter. The Z metric is comparable with a clinician-set specified false alarm rate (e.g., constant false alarm rate) to determine whether therapy should be provided. The FAR is set by the clinician without having to know detailed information regarding a threshold value for a physiological parameter. Further, the FAR is input by the clinician and used in this method without knowledge of any statistics for a distribution of a physiological parameter. The FAR is determined without relying on the underlying statistics for physiological parameter distribution to determine a threshold. Setting a threshold based on the physiological parameter can be avoided because the probability distribution function (e.g., $p(x_i|H_0)$) provides a measure of the instantaneous probability of false alarm for each measurement of the physiological parameter without the need for an individual threshold based on the physiological parameter. In another example, the non-event measurements that do not exceed the threshold are used in the probability distribution function to determine the instantaneous probability any individual measurement indicates an event (e.g., heart failure).

Figure 5:
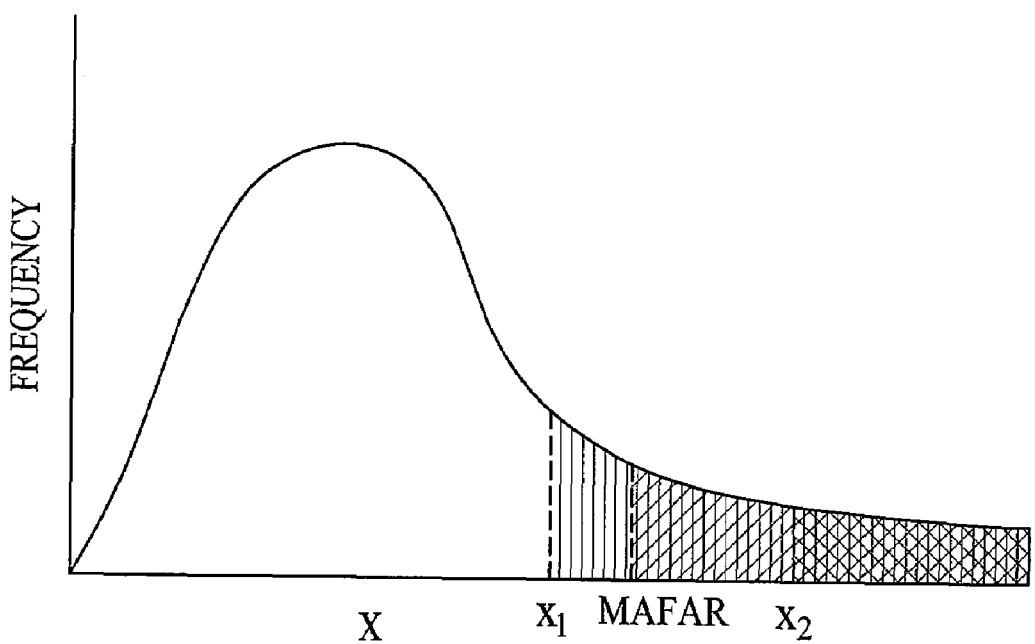
FIG. 5 is a plot showing the example of the non-event probability distribution function with a threshold tail area corresponding to a specified false alarm rate (FAR).

FIG. 5 shows another technique, which plots the specified false alarm rate (FAR) provided by the clinician as a threshold tail area corresponding to an instantaneous probability along the probability distribution function $p_j(x|H_0)$. The FAR of 30 false alarms every 365 days, described in the example above, would have a corresponding instantaneous probability of 8.2 percent (0.082), i.e., a threshold tail area of 8.2 percent. In one example, the measurement $x_1$, shown in FIG. 5, has a corresponding tail area (i.e., instantaneous probability of false alarm) determined by the equation:

$$C_1 = \int_{x_1}^{\infty} p_1(x|H_0)dx$$

The tail area for the measurement $x_1$ corresponds to a confidence $C_1$ (i.e., an instantaneous probability of false alarm). Because, in this example, the confidence ($C_1$) of the measurement $x_1$ is less than the threshold tail area corresponding to the FAR, an event or condition is declared to have occurred and a responsive alert or therapy is provided. In another example, multiple measurements are used to generate a confidence, as described below. The use of multiple measurements provides increased reliability by basing the determination of a detected event on more than a single measurement.

In yet another example, the measurement $x_2$ has a corresponding tail area determined by the equation:

$$C_2 = \int_{x_2}^{\infty} p_2(x|H_0)dx$$

Similar to the measurement $x_1$, the tail area for the measurement $x_2$ corresponds to a confidence $C_2$. In the example shown in FIG. 5, because the confidence ($C_2$) of the measurement $x_2$ is greater than the threshold tail area corresponding to the FAR, the event or condition is declared to not have occurred and, therefore, a responsive alert or therapy is not provided. Optionally, the FAR is equated with the tail area integration and the equation is solved for the FAR-corresponding threshold value of the physiological parameter. In such an example, an event or condition is declared to have occurred and a responsive alert or therapy is provided, for instance, for a physiological parameter measurement that exceeds the FAR-corresponding threshold value of the physiological parameter.

Figure 6:
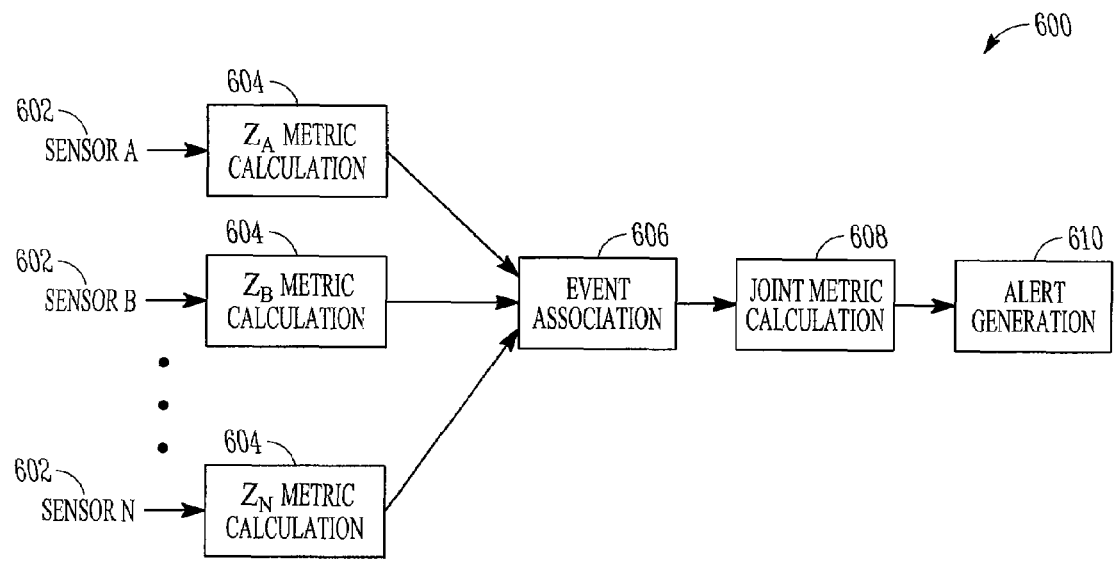
FIG. 6 is a block diagram showing one example of a multi-sensor event detection system.

FIG. 6 shows an example of a multi-sensor event detection system 600. In this example, the system 600 includes at least two or more sensors. In the example of FIG. 6, the system 600 includes sensors A to N (elements 602). Each sensor is configured to measure at least one physiological parameter. For instance, where the event detection system 600 is configured to detect heart failure, the sensors 602 variously detect, for example, heart sounds (e.g., S3 amplitude), DC impedance near the lungs, heart rate, respiration rate, weight, intracardiac pressure, or the like. In certain examples, the sensors 602 are included in the implantable medical device 102 of FIG. 1. In another example, the sensors are included in an external system 106. Optionally, the sensors 602 are distributed between both the implantable medical device 102 and the external system 106. The sensors typically collect recurring or periodic measurements of the physiological parameters, which may take on values that indicate the occurrence of a particular event (e.g., heart failure, decompensation, ischemia, or the like). The collected measurements are typically stored in at least one of the implantable medical device 102 and the external system 106, such as for generating one or more probability distribution functions, such as $p_i(x|H_0)$ and $p_j(x|H_0)$, as described above. In this example, the physiological parameters are uncorrelated and independent from each other while the sensors are collecting non-event measurements for generating the probability distribution functions. As described below, event-related measurements are typically excluded from the measurements used to generate the probability distribution functions, because event-related measurements of physiological parameters may be dependent on or correlated to one another, which can skew the probabilities of false alarm for each sensor.

In certain examples, each measurement from the sensors A to N is sent to corresponding individual Z metric calculation modules 604. The Z metric calculation modules 604 use the corresponding probability distribution functions for each physiological parameter to determine the corresponding Z metric for the individual measurements (described above). The Z metric value corresponds to the instantaneous probability that the measurement for a particular sensor is a false alarm (i.e., a confidence that the measurement is a false alarm). In the example of FIG. 6, there are multiple Z metrics, corresponding to each sensor, $Z_A$ through $Z_N$. An example of the Z metric equation is shown below for $Z_A$.

$$Z_{X_A} = -\mathrm{Log}_{10}\left[\int_{x_A}^{\infty} p_A(x|H_o)dx\right]$$

In another example, the $Z_B$ metric equation is for a negative tailed distribution (e.g., for DC impedance) for instance:

$$Z_{X_B} = -\mathrm{Log}_{10}\left[\int_{-\infty}^{x_B} p_B(x|H_o)dx\right]$$

The Z metrics are transformed with the logarithm, optionally, so the clinician may observe the significance between the $Z_N$ metric values. Using the logarithm transformation ensures the metric values are whole numbers and differences between the metric values are thereby easily observable. In one example, the transformation allows the clinician to identify trends in the metrics for the various physiological parameters that are otherwise difficult to observe when the untransformed confidences are examined. The Z metric calculation modules 604 are typically housed in at least one of the external device 106 and the implantable medical device 102, in certain examples.

Figure 7:
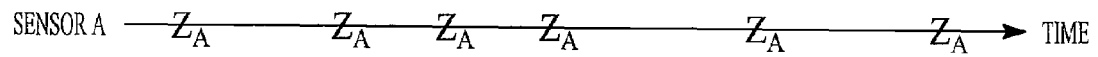
FIG. 7 is a schematic diagram showing one method for associating measurements from multiple sensors.
Figure 7:
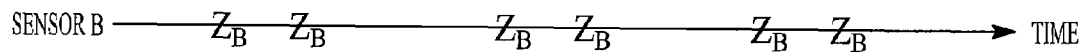

In the example of FIG. 6, the Z metrics are output to an event association module 606, such as to group the Z metrics with each other. Because each sensor typically takes multiple measurements, which may occur at differing intervals with respect to the other sensors, logic or signal processing is typically used to associate contemporaneous Z metrics with each other. Such logic or signal processing relates a single Z metric for each physiological parameter with other generally contemporaneous Z metric values for differing physiological parameters taken around the same time. For example, FIG. 7 shows sensors A and B with a time sequence of metric updates $Z_A$ and $Z_B$, respectively, shown along time lines. The metric updates for sensor A occur at different times than those for sensor B. Logic or signal processing is provided to associate the contemporaneous metric updates $Z_A$ with $Z_B$. In certain examples, the most recent metric $Z_A$ is associated with the most recent metric $Z_B$, nearest temporal neighbor measurement, and the like. The event association module 606 (FIG. 6) is typically included in at least one of the implantable medical device 102 and the external system 106.

In the example of FIG. 6, once the Z metric values for the sensors 602 are associated with each other, the associated Z metrics are sent through the joint metric calculation module 608. In certain examples, the associated Z metric values are additively combined into a joint metric J, as follows:

$$J = Z_A + Z_B + \ldots + Z_N$$

The joint metric J is then compared with a threshold value that established using information provided by a clinician. The threshold value is typically based on a clinician-specified constant predetermined false alarm rate (FAR) (e.g., constant false alarm rate). The joint metric J provides a convenient way to compare the values corresponding to the confidences generated with the equations described above to a single FAR-based threshold. If the joint metric J exceeds such threshold, an event or condition is declared to have occurred, and a responsive alert or therapy is typically provided. In certain examples, the threshold is a value proportional to a specificity desired by the clinician. For instance, if the patient is susceptible to a condition (e.g., has shown precursor symptoms, has a history of condition and the like) the clinician would likely set a low threshold to ensure that a patient at higher risk of the condition is provided therapy. In another example, where the patient is unlikely to experience the condition (e.g., the patient has a combination pacemaker/defibrillator, but is not expected to experience heart failure) the clinician would set a high threshold to ensure that the low risk patient is only treated where measurements indicate there is a high probability of the onset of the condition (i.e., a low probability of a false alarm).

As described above, in certain examples, the FAR set by the clinician is converted as shown below to generate a threshold that is comparable with the joint metric J.

$$\text{Threshold} = -\text{Log}_{10}(FAR)$$

The joint metric J corresponds to the combined $Z_N$ metric values determined from the confidences generated for the measurements of the physiological parameters, as described above (i.e., the instantaneous probability of a false alarm for the measurement $x_i = k$). The logarithms used with the FAR and the $Z_N$ metric values convert the confidences and the FAR into observable values (i.e., whole numbers). Optionally, other functions are used to compare the FAR and the confidences including, but not limited to, other logarithms (e.g., natural) and the like. In another example, without using the logarithm function, the joint metric J is a value that may appear insignificant to a clinician because the following function is used to produce the joint metric.

$$J = 1 - (C_1 * C_2)$$

Because the confidences generated are less one, the joint metric J will necessarily have a value less than one. It may therefore be difficult for a clinician to observe differences in the joint metric J and the confidences $C_1$ or $C_2$ over time. The addition of the logarithm transformation enhances the ease with which a clinician may follow trends of the metrics $Z_N$ and the joint metric J while continuing to allow comparison of the joint metric J with the threshold.

After the FAR is converted to the Threshold value, the Threshold and joint metric J are compared, in a similar manner as described above with the single metric. For instance, if the FAR is specified by the clinician to be one false alarm every 365 days, then, in one example, the corresponding Threshold generated with the above equation is 2.56. In another example, if the measurement $x_A = k$ for a first sensor 602 provides an eight percent (0.08) instantaneous probability the measurement is a false alarm (see the example $C_i$ equations above), the corresponding $Z_A$ metric is approximately 1.10. Similarly, for instance, if the measurements for second and third sensors 602 provide five percent and two percent probabilities of false alarm, respectively, the corresponding $Z_B$ and $Z_C$ metrics are 1.30 and 1.70. In this example, the joint metric J for the additively combined $Z_A$, $Z_B$ and $Z_C$ metrics is 4.10. Because, in this example, the joint metric J=4.10 is greater than the Threshold of 2.56, an event or condition is declared to have occurred, and a responsive alert or therapy initiation or adjustment is provided (e.g., alert generation 610).

The assumption of independence and the simple addition of confidences $Z_i$ to arrive at the joint confidence metric J results in a small bias, in one example. This bias is corrected by a simple correction factor that is a function of the number of elements used to compute J. In one illustrative example, the joint metric J normally is equal to the following:

$$J = \left( \sum_{i=1}^{N} Z_i \right)$$

If it is assumed N=10, and the metrics are truly independent, and if each measures exactly the mean value $C_i = 0.5$, then each $Z_i$ metric will have a value (after taking a logarithm) of 0.3. When the N=10 metrics $Z_i$ are summed, the joint metric J=3.0, which implies an instantaneous probability of false alarm of $10^{-3}$ (0.1 percent). This appears counterintuitive. If each sensor returns the mean value, the joint probability of false alarm should be 0.5. To correct for this bias, a fixed correction factor of 0.3 is applied to each additional $Z_i$ beyond the first (i.e., i=1). The joint metric J with bias correction is thus computed as:

$$J = \left(\sum_{i=1}^{N} Z_i\right) - 0.3(N-1)$$

For the previous example, with the correction factor applied the joint metric J=0.3, which correctly implies a 0.5 (50%) instantaneous false alarm probability.

After the FAR is converted to the Threshold value, the Threshold and joint metric J are compared, in a similar manner as described above with the single metric. For instance, if the FAR is specified by the clinician to be one false alarm every 365 days, then, in one example, the corresponding Threshold generated with the above equation is 2.56. In another example, if the measurement $x_A$=k for a first sensor 602 provides an eight percent (0.08) instantaneous probability the measurement is a false alarm (see the example $C_i$ equations above), the corresponding $Z_A$ metric is approximately 1.10. Similarly, for instance, if the measurements for second and third sensors 602 provide five percent and two percent probabilities of false alarm, respectively, the corresponding $Z_B$ and $Z_C$ metrics are 1.30 and 1.70. In this example, the joint metric J for the additively combined $Z_A$, $Z_B$ and $Z_C$ metrics is 4.10. Because, in this example, the joint metric J=4.10 is greater than the Threshold of 2.56, an event or condition is declared to have occurred, and a responsive alert or therapy initiation or adjustment is provided (e.g., alert generation 610). Optionally, where at least some of the Z metrics are not strictly independent, those Z values are weighted downward, for instance by a multiplier less than one to account for the partial absence of independence. This multiplier is applied to each of the metrics that are dependent upon other metrics to some extent.

As described above, under certain physiological conditions (e.g., depending on sleep state, activity state, posture, etc.), corrupted sensors and the like, measurements may be regarded as invalid, such that they should be excluded from the joint metric J calculation and comparison with the Threshold. In certain examples, if measurements for a first physiological parameter vary widely from event-related indications being provided by various other physiological parameters, such measurements from that particular sensor may be excluded from the joint metric J calculation. In certain examples, measurements regarded as invalid are set to a constant value that provides a negligible influence to the joint metric J. For instance, a 90 percent (0.9) instantaneous probability of a false alarm and corresponding Z metric value of 0.5 negligibly influence the joint metric J. In certain examples, reducing or minimizing the impact of corrupted sensors or invalid measurements allows the event detection system to continue functioning based on other measurements or other sensors associated with other physiological parameters.

The joint metric J provides a composite value corresponding to the probabilities of false alarm for a variety of physiological parameters. It permits information from multiple sensors 602 to be compiled and used to make the event or condition detection determination and responsive alert or therapy decision. The joint metric J is comparable with the single clinician-set constant predetermined false alarm rate (FAR), such as to determine whether a responsive alert or therapy should be provided. The FAR can advantageously be set by the clinician without knowing detailed information regarding appropriate threshold values for multiple physiological parameters. Setting thresholds based on the physiological parameters is avoided because the probability distribution functions (e.g., $p(x_i|H_0)$) provide measures of the probabilities of false alarm for each measurement of the physiological parameters without the need for an individual threshold for each parameter. In certain examples, the non-event measurements are used in the probability distribution function to determine the instantaneous probability any individual measurement indicates an event or condition (e.g., heart failure), thereby avoiding the need for establishing individual predetermined thresholds for each physiological parameter.

In other examples, the probability distribution function for a set of N measurements from multiple sensors is an N-dimensional function $p(x_1, x_2, x_3, \ldots, x_N|H_0)$. In practice, multidimensional distributions are difficult to estimate from limited data, and are computationally cumbersome. The examples described above, provide a framework for a multi-sensor constant false alarm rate (CFAR) system without the burden of multi-dimensional distribution functions. This is facilitated by assuming statistical independence of the sensor measurements, thereby providing a convenient and manageable univariate distribution framework. Thus, each sensor (or information source) is modular, and can be added or removed from the system without affecting the other sensor subsystems, as described above. Sensors are added or removed at will from the detection decision chain, either automatically depending on quality and reliability of the produced measurements, or manually based on the decision of the clinician as deemed appropriate for each patient. The physiologic event detection threshold (achieved through the specified constant false alarm rate) can remain the same regardless of the number of sensors available.

Figure 8:
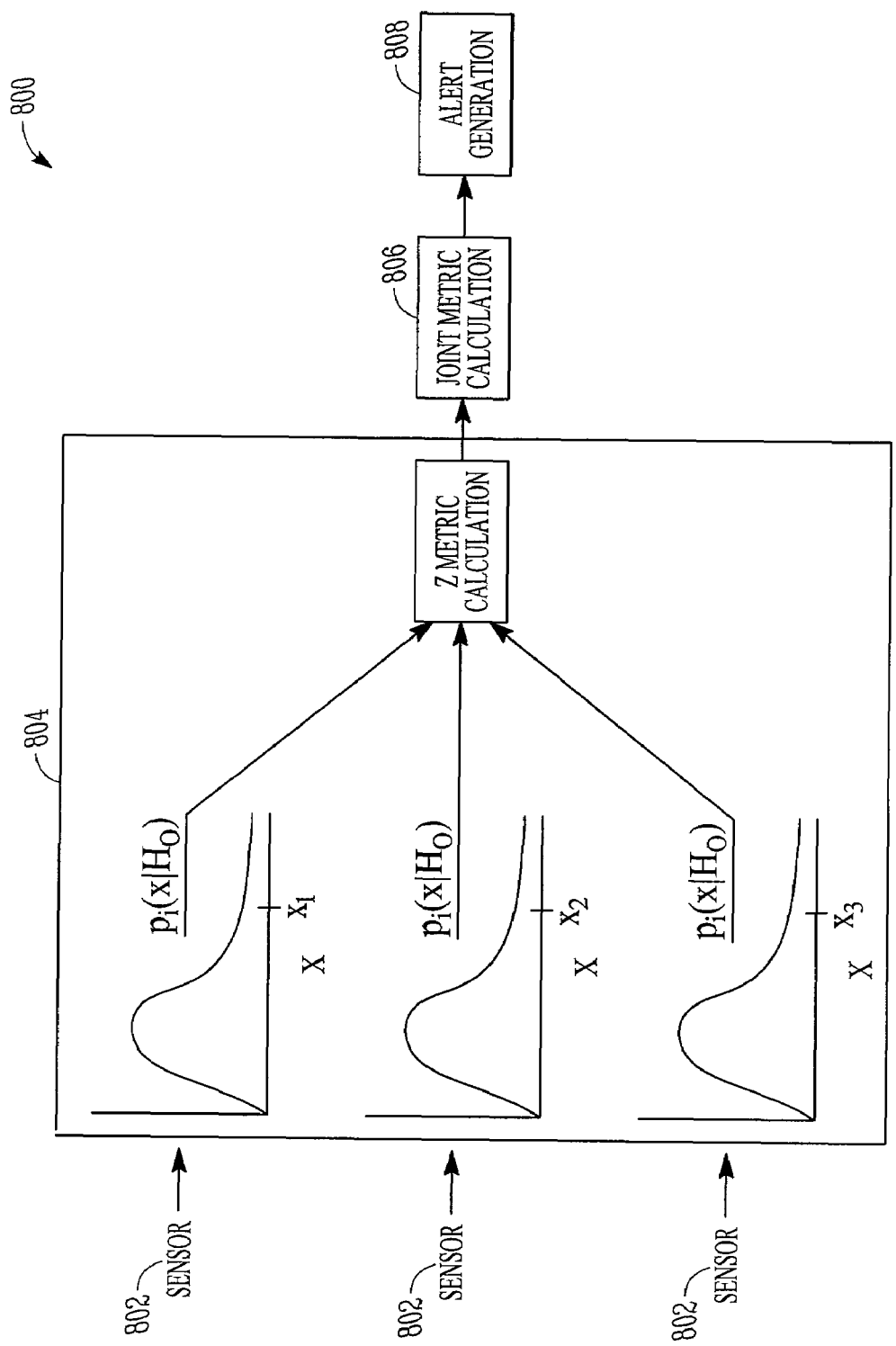
FIG. 8 is a block diagram showing one example of a single-sensor composite measurement event detection system.

FIG. 8 shows an example of a single sensor composite measurement event detection system 800. In the example of FIG. 8, the system 800 includes a sensor 802 configured to measure at least one physiological parameter. The sensor 802 is typically included in at least one of the implantable medical device 102 and external system 106, shown in FIG. 1. The sensor 802 collects recurring or periodic measurements of one or more physiological parameters that indicate the occurrence of a particular event or condition (e.g., heart failure, ischemia, etc.). The collected measurements are stored in at least one of the implantable medical device 102 and the external system 106 and are used to generate a probability distribution function, such as $p_i(x|H_0)$ as described above. The sensor typically collects non-event measurements for generating the probability distribution function. As previously described, event-related measurements are typically excluded from the measurements used to generate such a probability distribution function because such event-related measurements of physiological parameters could skew the probabilities of false alarm for the sensor 802.

In certain examples, measurements $x_i$ from the sensor 802 are sent to a Z metric calculation module 804. The Z metric calculation module 804 uses the probability distribution function associated with the physiological parameter to determine the corresponding Z metric for the individual measurements (described above). The Z metric values correspond to the instantaneous probability that the measurement for the sensor 802 is a false alarm (i.e., a confidence the measurement is a false alarm). An example of the Z metric equation is shown below for $Z_1$.

$$Z_i = -\text{Log}_{10}\left[\int_{x_1}^{\infty} p_i(x|H_o)dx\right]$$

The Z metric calculation module 804 is typically housed in at least one of the external device 106 and the implantable medical device 102, and can be implemented using a microprocessor or other suitable circuit.

After the Z metric values are generated for the measurements $x_i$, the associated Z metrics are sent through the joint metric calculation module 806. The associated Z metric values are typically additively combined into a joint metric J, as shown in the equation below.

$$J = Z_i + Z_j + \ldots + Z_{x_N}$$

As described above with the multi-sensor system 600, the joint metric J is then compared with a threshold that is typically established using information provided by a clinician. The threshold is typically based on a clinician-specifiable FAR. The joint metric J provides a convenient way to compare the values corresponding to the confidences generated with the equations described above to a single FAR-based threshold. If the joint metric J exceeds this threshold, an event or condition is declared to have occurred, and a responsive alert or therapy is typically provided (e.g., alert generation 808). In certain examples, the threshold is a value proportional to a specificity desired by the clinician. The FAR is set by the clinician without having to know detailed information regarding a threshold value for a physiological parameter. Further, the FAR is input by the clinician and used in this method without knowledge of any statistics for a distribution of a physiological parameter. The FAR is determined without relying on the underlying statistics for physiological parameter distribution to determine a threshold.

In certain examples, the FAR set by the clinician is converted as shown below to generate a Threshold comparable with the joint metric J.

$$\text{Threshold} = -\text{Log}_{10}(FAR)$$

The joint metric J corresponds to the combined Z metric values determined from the confidences generated for the measurements of the physiological parameters, as described above (i.e., the instantaneous probability of a false alarm for the measurement $x_i = x_1, x_2, x_3$ etc.). After the FAR is converted to the Threshold value, the Threshold and joint metric J are compared, in a similar manner as described above with respect to the multi-sensor system 600. For instance, where the FAR is one false alarm every 365 days, in one example, the corresponding Threshold generated with the above equation is 2.56. In another example, if the measurement $x_i = x_1$ for the sensor 802 provides an eight percent (0.08) instantaneous probability the measurement is a false alarm (see the example $C_i$ equations above), the corresponding $Z_1$ metric is approximately 1.10. Similarly, for instance, if the second and third measurements for the sensor 802 provide five percent and two percent probabilities of false alarm, respectively, the corresponding $Z_2$ and $Z_3$ metrics are 1.30 and 1.70. The resulting joint metric J for the additively combined $Z_1$, $Z_2$ and $Z_3$ metrics is 4.10. Because the joint metric J exceeds the Threshold value, an abnormal event or condition is declared to have occurred, such that a responsive alert or therapy can be provided.

The Z metric calculation module 804 may perform Z metric calculations at set ongoing time intervals, such as continuously from measurement-to-measurement, hourly, daily, or the like. In certain examples, the Z metric calculations use one or more statistical measures, such as a mean, median, or the like, as applied to multiple measurements taken over a particular time period. In such examples, the Z metric values corresponding to one or more such statistical measures can be used in the joint metric J calculation. In certain examples, the Z metric values are stored, such as for a specified time period. The stored Z metric values can be occasionally or regularly combined, such as to form the joint metric J in the module 806. In certain examples, Z metric values that have been stored for a specified time period (e.g., the oldest Z metric values) are removed from the joint metric J determination, and more recent Z metric values are used.

Figure 9:
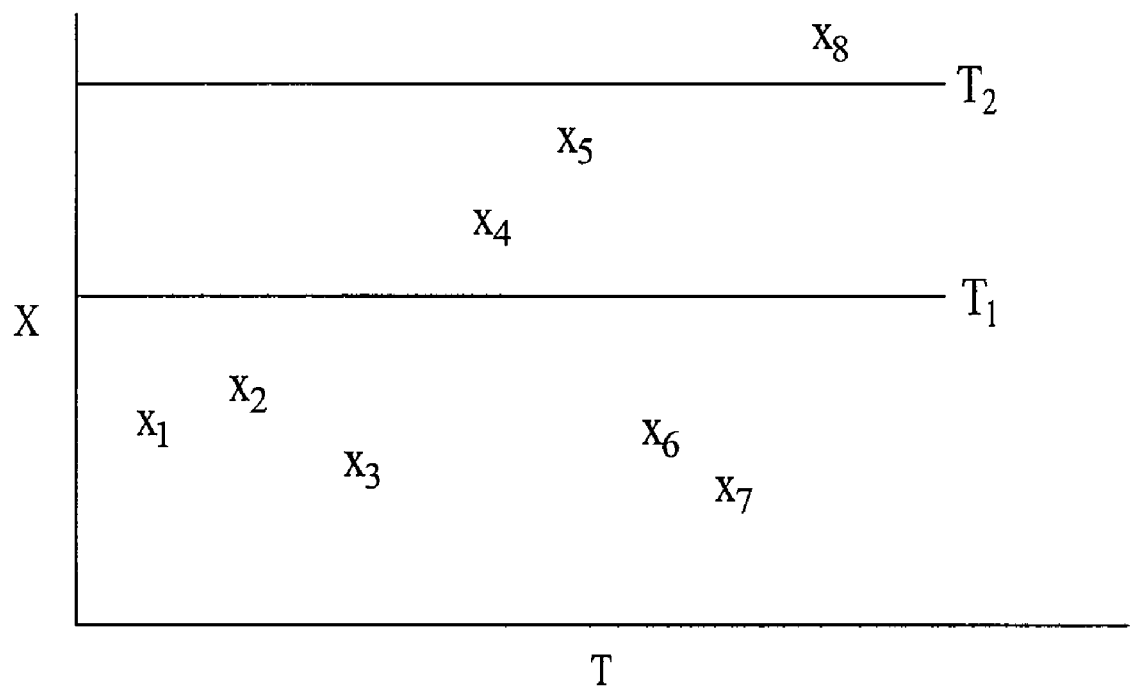
FIG. 9 is a plot showing another example of constant false alarm event detection for a physiological parameter.

FIG. 9 shows another example of constant false alarm event detection system for a physiological parameter. In this example, a first distribution of measurements is collected for a first physiological parameter, such as described above (i.e., with a sensor of the implantable medical device 102 and/or external system 106). Non-event measurements are typically collected to generate a probability distribution function (e.g., $p_i(x|H_0)$). In one example, only measurements from before a predetermined period of time prior to the latest measurement are included in the probability distribution function. Limiting inclusion of recent measurements in the probability distribution function provides a guard band that assists in preventing the inclusion of possible event date in the distribution. At least one composite measurement ("CM") is generated from the probability distribution function. In certain examples, the composite measurement is the median value of multiple measurements. In another example, the CM includes, a mean, a specified percentile measurement of the distribution, a variance or multiple thereof, a standard deviation or multiple thereof, or the like.

In this example, the composite measurement, CM, is typically used to determine a threshold. In certain examples, the composite measurement CM is adjusted by a constant k. For instance, the composite measurement is multiplied by a constant k, which is typically greater than one, to generate the threshold, such as shown in the below equation.

$$T = k * CM$$

Measurements of the physiological parameter $x_i$ that exceed the threshold value may indicate the detection of an event or condition, as described further below. In certain examples, the base composite measurement (without adjustment by a scaling or other constant) is used as the threshold, such as where the composite measurement includes, for instance, a percentile value of the probability distribution function (e.g., $80^{th}$ percentile) that is deemed rare enough to indicate the occurrence of an event or condition. In certain examples, the most recent non-event measurements used in the probability distribution function are weighted more heavily (e.g., by double counting, scaling, etc.) to place the most emphasis on the particularly recent measurements. As an illustrative example, measurements taken within the last three days could be double counted to more greatly influence the composite measurements and corresponding thresholds.

Measurements of the physiological parameter (e.g., heart sound amplitude, DC impedance, or the like) are typically compared against the threshold. If the physiological measurement exceeds the threshold value, then that measurement is counted. The clinician typically sets a specified false alarm rate (FAR), such as based on a desired false alarm rate, specificity, or sensitivity. For example, in a situation where the patient is known to be susceptible to a condition (e.g., has shown precursor symptoms, has a history of condition and the like) the clinician would likely set a lower threshold (accepting more false alarm) to ensure that a patient at higher risk of the condition receives more sensitive detection of that condition, such that a responsive alert or therapy can more readily be provided. In certain examples, the clinician sets the FAR such that an event or condition is if the count has four or more measurements that exceed the threshold during any five day period. In another example, such as where the patient is unlikely to experience the condition (e.g., the patient has a combination pacemaker/defibrillator, but is not expected to experience a heart failure condition) the clinician would set a high specificity to ensure that the low risk patient is only treated if one or more measurements indicate that there is a high probability that the event or condition (e.g., heart failure) has been detected. In another illustrative example, the clinician sets the FAR to provide an alert and therapy if the count has two or more measurements that exceed the threshold in any two day period.

The FAR is set by the clinician without knowing detailed information regarding a threshold value for a physiological parameter. Further, the FAR is input by the clinician and used in this method without knowledge of any statistics for a distribution of a physiological parameter. The FAR is determined without relying on the underlying statistics for physiological parameter distribution to determine a threshold.

In certain examples, multiple thresholds are set, such as to provide a variety of responsive alerts or therapies for measurements of the physiological parameter that exceed the various thresholds. For instance, in the example of FIG. 9, a first threshold $T_1$ and a second threshold $T_2$ are provided. In certain examples, the first threshold $T_1$ is generated by adjusting the composite measurement CM by a first constant $k_1$ and the second threshold is generated by adjusting the composite measurement CM by a second greater constant $k_2$.

$T_1 = CM * k_1$ $T_2 = CM * k_2$ $k_1 < k_2$

In certain examples, a first $FAR_1$ is associated with the first threshold $T_1$ and a second $FAR_2$ is associated with the second threshold $T_2$. The specified false alarm rates and the corresponding thresholds can be established to facilitate rapid recognition (and alert or treatment) of a condition indicated by prominent or moderate changes in the physiological parameter. For instance, $FAR_1$ can be set to provide a high sensitivity and low specificity, such that an abnormal event or condition is declared when relatively fewer measurements exceed a lower threshold $T_1$ during a particular time period; the $FAR_2$ is set to provide a low sensitivity and high specificity, such that an abnormal event or condition is declared when relatively more measurements exceed the higher threshold $T_2$ over the particular time period. Setting a variety of predetermined false alarm rates facilitates rapid recognition (and alert or treatment) of a condition indicated by a prominent change in the physiological parameter, and provides more conservative recognition (and alert or treatment) for a condition indicated by a more moderate change in the physiological parameter. The false alarm rates are set by the clinician without having to know detailed information regarding a threshold value for a physiological parameter. Further, the false alarm rates are input by the clinician and used in this method without knowledge of any statistics for a distribution of a physiological parameter. The false alarm rates are determined without relying on the underlying statistics for a physiological parameter distribution to determine a threshold. In this example, the thresholds are based on the statistics of the physiological parameter distribution and the false alarm rates are distinct from the threshold and, as described above, independent of the distributions and statistical measurements thereof (e.g., mean, standard deviation, percentiles and the like).

In an illustrative example, the clinician sets the $FAR_1$ to provide an alert when the count has M measurements within an N period of time, such as four or more measurements $x_i$ (i.e., M) in five days (i.e., N) that equal or exceed the threshold $T_1$, and $FAR_2$ is set to provide an alert when the count has one or more measurements that equal or exceed the threshold $T_2$ in two days. Assuming that the illustrative example of FIG. 9 depicts a five day time period, and assuming the above described settings of $FAR_1$ and $FAR_2$, an event or condition would not be declared using $FAR_1$ because only three measurements $x_4$, $x_5$ and $x_8$ exceed $T_1$. However, an alert is provided using $FAR_2$ because one measurement $x_8$ exceeds $T_2$. In another example, the guard band described above, is set proportionally to the N period of time to help ensure the probability distribution does not include possible event data.

In another example, similar to determining a confidence as described above, a value corresponding to a confidence is determined for each measurement that exceeds a threshold such as, $T_1$ and/or $T_2$. These confidences are accumulated for a period of time N, and if the accumulated confidences exceed a specified false alarm rate (described above), an alert is provided, and in one example, therapy is delivered.

When a threshold is established by computing a probability distribution function using non-event data, it adapts to gradual non-event changes in the physiological parameter over time. While this may be desirable, in certain circumstances, in other circumstances it may be undesirable. An alternative approach is to compute a static threshold for a particular patient using non-event data, instead of an adaptive threshold. The static threshold would typically not be recomputed without clinician or other intervention. Another approach is to use both a static threshold and an adaptive threshold. In such an example, even if the adaptive threshold has not been triggered because of the gradual nature of the change in the physiological parameter, a secondary static threshold may still result in the declaration that an abnormal event or condition has occurred. Using a secondary static threshold, therefore, provides a safety measure that may be desirable under certain circumstances.

Figure 10:
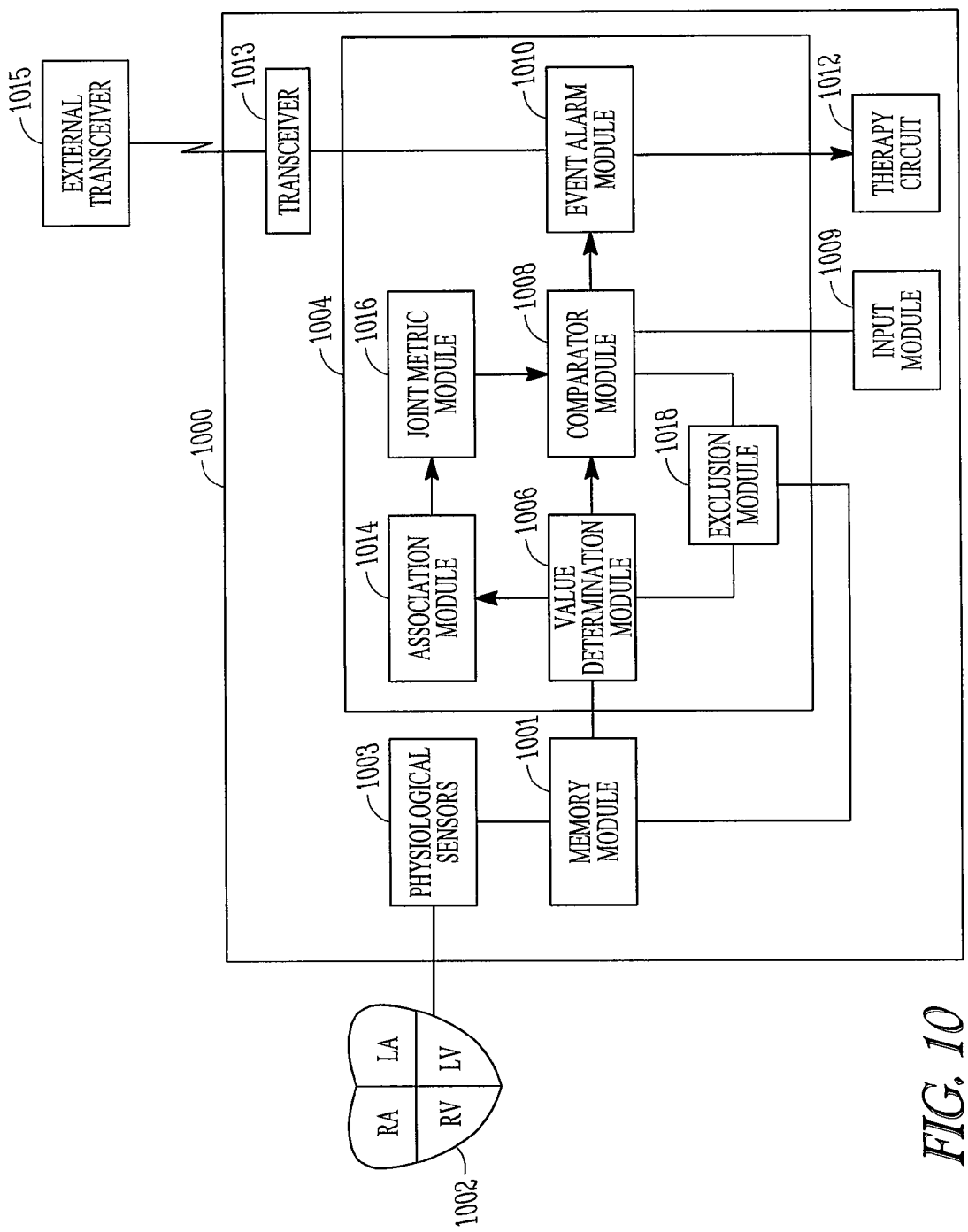
FIG. 10 is a schematic diagram showing one example of an event detection system.

FIG. 10 is a schematic diagram showing an example of an event detection system 1000. In this example, the system 1000 typically includes the implantable medical device 102 (FIG. 1). The implantable medical device 102 is typically accompanied by an external system 106, such as an external programmer, remote server, repeater, other communication device or the like, such as shown in FIG. 1. The implantable medical device 102 may include an implantable cardiac function management device, which may include a pulse generator or other electronics unit coupled to a heart 1002, such as with an electrode or lead system 106 or otherwise adapted to sense heart signals or provide therapy to the heart 1002.

In the example of FIG. 10, the event detection system 1000 includes at least one physiological sensor 1003 adapted to collect at least the first distribution of measurements for a first physiological parameter, such as described above. In certain examples, the physiological sensor 1003 includes, but is not limited to, the lead system 104, and can be included within a portion of the implantable medical device 102, a portion of the external system 106, and the like. The physiological sensor 1003 typically measures one or more physiological parameters including, but not limited to, heart sounds, heart rate, intracardiac pressure, thoracic or intracardiac or other impedance, or the like. In certain examples, the event detection system 1000 includes multiple physiological sensors 1003, such as to measure a plurality of different physiological parameters.

Information about measurements from the physiological sensor 1003 (e.g., lead system 104, implantable medical device 102 and the like) is typically sent to a memory module 1001 for storage, such as for computing at least one probability distribution function, such as $p_i(x|H_0)$, $p_j(x|H_0)$, or the like. In certain examples, the memory module 1001 stores physiological measurements for one or more other purposes. In certain examples, stored measurements deemed corrupt, invalid (e.g., because confounded by one or more other physiological parameters, or because they relate to a measured event or condition, or because they are associated with a malfunctioning sensor, etc.), etc. are stored, but are not used to compute the probability distribution function.

In the example of FIG. 10, the event detection system 1000 includes a processor circuit 1004 that receives measurements of at least one physiological parameter, such as the memory module 1001 or the at least one physiological sensor 1003. The processor circuit can be included in one or both of the implantable medical device 102 and the external system 106. The processor circuit 1004 typically includes a value determination module 1006 adapted to determine one or more values corresponding to at least a first area of the first distribution from a measurement of the first physiological parameter toward an end point of the distribution, as described above. A comparator module 1008 is typically included in the processor circuit 1004 and in communication with the value determination module 1006. The comparator module 1008 compares the one or more values with a specified threshold that is based on a false alarm rate (FAR) provided, for instance, by the clinician (described above), or by a default (e.g., manufacturer-programmed) value. In one example, the FAR is input by the clinician through an input module 1009. The input module, optionally includes, but is not limited to, a touch screen, keypad, keyboard, voice recognition sensor, receiver and the like.

The processor circuit 1004 typically includes an event or condition determining module, such as event alarm module 1010, in communication with the comparator module 1008. The event alarm module 1010 is adapted to provide a responsive indication or alert if the measurement is declared to be representative of a detected abnormal event or condition using the comparison performed by the comparator 1008. In certain examples, the event alarm module 1010 provides notification of a detected abnormal event or condition to a therapy circuit 1012, such as for initiating, adjusting, or otherwise providing a responsive therapy, such therapy to the heart 1002. In certain examples, the event detection system 1000 includes a transceiver 1013 in communication with at least the event alarm module 1010. The transceiver 1013 typically transmits and/or receives data to or from an external transceiver 1015 or other location. In certain examples, the transceiver 1013 is in the implantable medical device 102 and the external transceiver 1015 is in the external system 106. In certain examples, the transceiver 1013 is in the external system 106 and the external transceiver 1015 is in the implantable medical device 102. The external system 106 can include the processor circuit 1004, such as for determining and sending information such as one or more alerts or therapy instructions to the implantable medical device 102.

In certain examples, the processor circuit 1004 includes an association module 1014 in communication with the value determination module 1006. The association module 1014 typically collects values from multiple physiological sensors 1003, which can take their measurements at differing intervals. Logic or signal processing in the association module 1014 typically relates a single value, for each physiological parameter, with one or more other substantially contemporaneous values for one or more other differing physiological parameters taken around that time. The association module communicates with a joint metric module 1016, in certain examples. The joint metric module 1016 combines different values from the association module 1014 into a joint metric, such as joint metric J, described above. In certain examples, the joint metric module 1016 combines multiple values corresponding to multiple measurements from the same physiological sensor 1003 (e.g., heart sound amplitude, etc.). The comparator module 1008 communicates with the joint metric module 1016, in certain examples. The comparator module 1008 typically compares the joint metric J with a specified threshold. As described above, the specified threshold is typically based on a predetermined false alarm rate (FAR), which can be specified by a clinician, such as to override a default value set by the system manufacturer. The event alarm module 1010 communicates with the comparator module 1008, such as to provide an indication of the occurrence of an abnormal event or condition (which can trigger a responsive alert or therapy) if the joint metric is deemed to be representative of a detected abnormal event or condition using the comparison performed by the comparator 1008. In certain examples, the event alarm module 1010 typically provides notification of a detected abnormal event or condition to a therapy circuit 1012, such as for initiating, adjusting, or otherwise providing a responsive therapy, such as to the heart 1002 or elsewhere.

The processor circuit includes an exclusion module 1018, in certain examples. The exclusion module 1018 is useful to remove one or more measurements from the computation of the probability distribution function, such as measurements in the memory 1001 that correspond to a detected abnormal event or condition, any corrupt or confounded measurements, any old measurements, or the like. In certain examples, the measurements stored in the memory module 1001 for computing the probability distribution function are updated occasionally or periodically. In certain examples, the exclusion module 1018 typically removes measurements from the probability distribution function that are outside a most-recent or other moving window of time. In certain examples, the removed measurements are retained in the memory module 1001 for other uses, even though they are not used for computing the probability distribution function (e.g., for historical purposes, review by the clinician, other operations of the implantable medical device 102, or the like). If the comparator module 1008 indicates the occurrence of an abnormal event or condition for one or more measurements, such measurements are typically excluded from being used in computing the normal probability distribution function.

Figure 11:
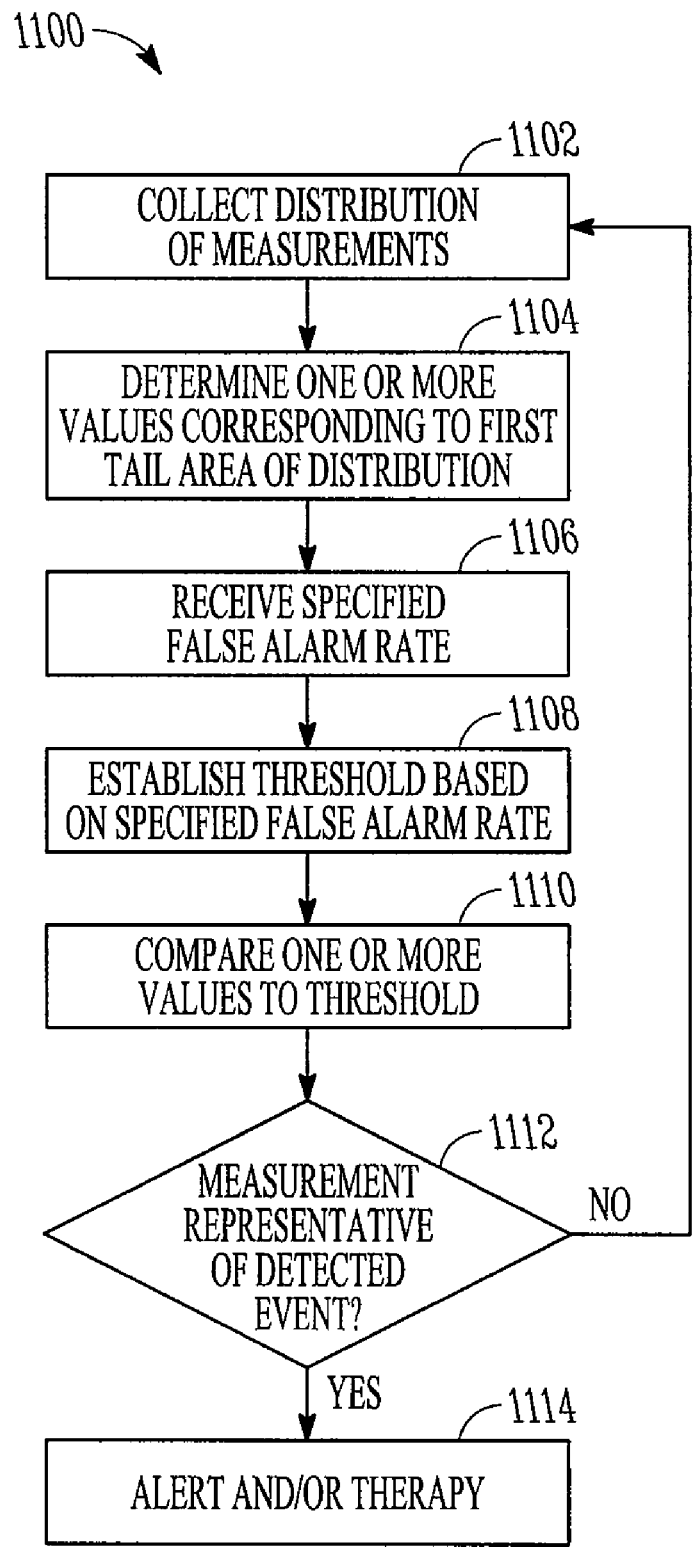
FIG. 11 is a block diagram showing one example of a Constant False Alarm Rate (CFAR) method for event detection using a non-event probability distribution function.

FIG. 11 is an example of a flow chart showing an example of an event detection method 1100. In the example of FIG. 11, at 1102, a first distribution of measurements for a first physiological parameter is collected. Illustrative examples of the first physiological parameter typically include, but are not limited to, cardiovascular parameters, such as heart sounds, heart rate, intracardiac pressure, thoracic impedance, weight, respiration rate, or the like. In examples, the first physiological parameter includes, but is not limited to a hormone level, a blood count, neural activity, muscle activity, or any other physiological parameter. At 1104, one or more values corresponding to at least a first tail area of the first distribution is determined. The area is typically determined from at least one measurement of the first physiological parameter toward an end point of the distribution. At 1106, a specified false alarm rate (FAR) is received. In one example, the false alarm rate is entered by the clinician through an input module, such as a keyboard, touch screen, keypad, receiver and the like. The FAR, in certain examples, is set by the clinician according to a desired false alarm rate, specificity, or sensitivity, or a default value can alternatively be provided by the manufacturer, if desired. The FAR is typically set using at least one of the implantable medical device, external system 106, or the like (FIG. 1). The FAR is set by the clinician without having to know detailed information regarding a threshold value for a physiological parameter. Further, the FAR is input by the clinician and used in this method without knowledge of any statistics for a distribution of a physiological parameter. The FAR is determined independently from the underlying statistics for the physiological parameter distribution to determine a threshold. At 1108, a specified threshold is established, such as by using the predetermined false alarm rate (FAR), as described above.

Referring again to FIG. 11, at 1110, the one or more values (described above), are compared with the specified threshold. At 1112, in certain examples, if the one or more values exceeds the predetermined threshold, then the corresponding measurement is considered indicative of a detected abnormal event or condition. At 1114, an alert and/or therapy is provided in response to a detected abnormal event or condition, such as by an implantable medical device 102. In certain examples, the implantable medical device 102 includes a cardiac function management device that may include an implantable pulse generator. Otherwise, process flow returns to 1102 if the one or more values fails to exceed the predetermined threshold. In one example, the non-event measurement of the first physiological parameter is then available to be included in an immediate or later re-computation of the first probability distribution of measurements at 1102.

Variations of the method 1100 are possible. For example, only non-event measurements are typically used for computing the first probability distribution at 1102. However, the method 1100 could include fitting the measurements of the first physiological parameter to at least one mathematically-specified distribution of a family of specified distributions, or using such a mathematically-specified distribution function without using actual patient and/or population-based measurements to compute the probability distribution function.

Determining the one or more values corresponding to the first tail area of the first distribution typically includes determining a first instantaneous probability of false alarm for the measurement of the first physiological parameter. In a heart failure detection example, determining the first instantaneous probability of false alarm for the measurement of the first physiological parameter includes determining a heart failure condition confidence for the measurement of the first physiological parameter.

The method 1100 may include updating the first distribution of measurements for the first physiological parameter. This may include collecting one or more additional measurements for the first physiological parameter, such as by ongoing collection and retention of measurements of the first physiological parameter taken within a most-recent or other moving window of time. The measurements may themselves include processing over time, such as finite impulse response (FIR), infinite impulse response (IIR) or other digital, analog, or mixed-signal filtering or processing. In certain examples, more recent measurements are weighted more heavily than earlier ones. Updating the first distribution of measurements for the first physiological parameter includes may include excluding corrupted, confounded, event-related, or otherwise invalid measurements.

In certain examples, determining one or more values corresponding to at least a first tail area of the first distribution (e.g., step 1104 above) includes determining a first value corresponding to the first tail area of the first distribution from a first measurement of the first physiological parameter toward an end point of the distribution, and determining a second value corresponding to a second tail area of the first distribution from a second measurement of the first physiological parameter toward an end point of the distribution. In certain examples, the first value is combined with the second value to form a joint metric. In certain examples, comparing the one or more values to the predetermined threshold includes comparing the joint metric to the predetermined threshold.

Figure 12:
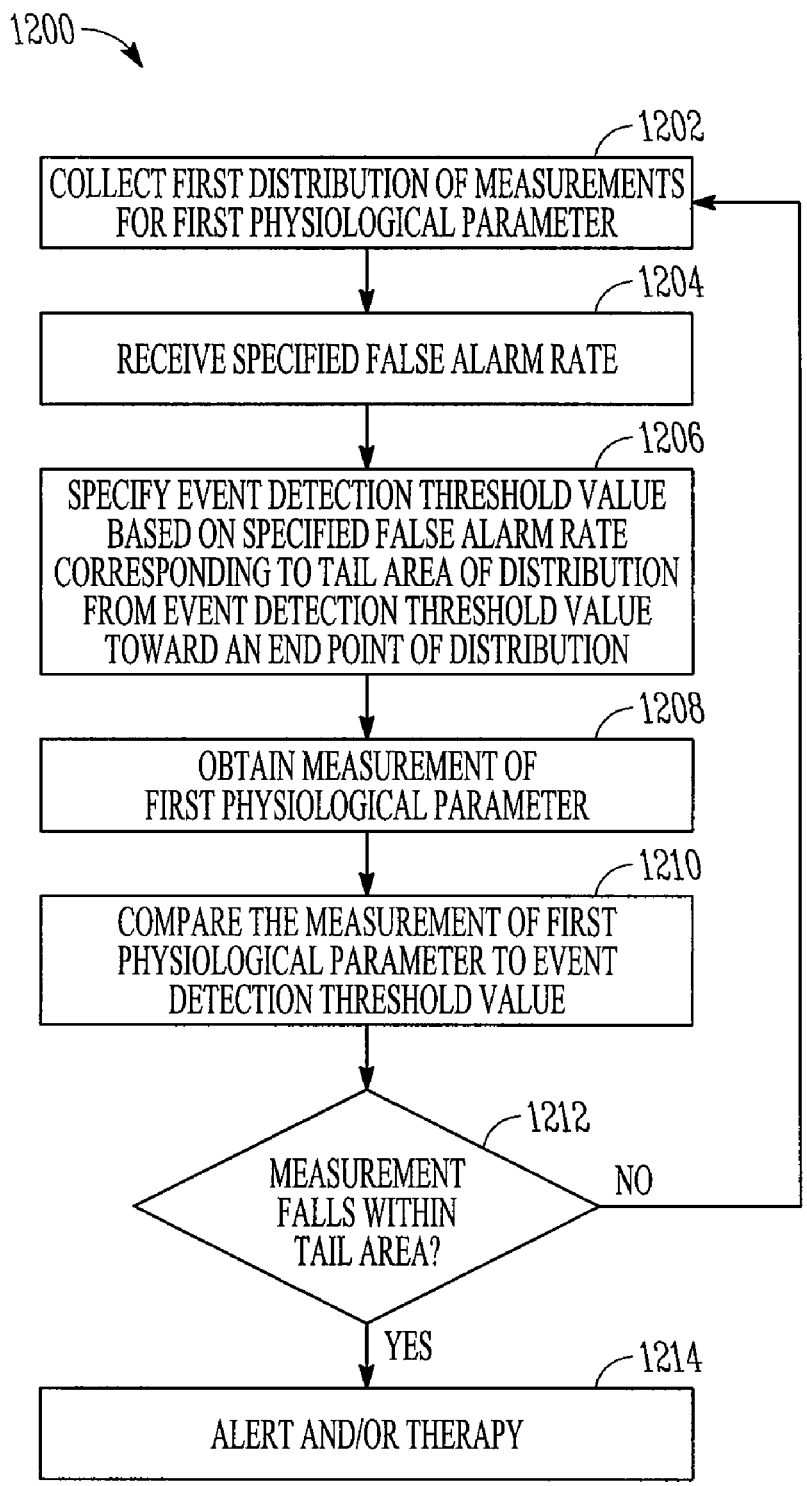
FIG. 12 is a block diagram showing another example of a Constant False Alarm Rate (CFAR) method for event detection using a non-event probability distribution function.

FIG. 12 is an example of a flow chart illustrating another example of an event detection method 1200. In the example of FIG. 12, at 1202 a first distribution representative of measurements for a first physiological parameter is generated, typically by using only non-event measurements. At 1204, a specified false alarm rate is received. In one example, the false alarm rate is input by a clinician through, but not limited to, a keyboard, keypad, touch screen, receiver and the like. At 1206, an event detection threshold value is specified that corresponds to the false alarm rate inputted to an implantable medical device (e.g., an implantable pulse generator), external system and the like. The event detection threshold value is typically computed using the specified predetermined false alarm rate. The event detection threshold value corresponds to a first tail area of the first distribution extending from the event detection threshold value toward an end point of the first distribution. At 1208, a measurement of the first physiological parameter is detected. At 1210, the measurement of the first physiological parameter is compared to the event detection threshold value. At 1212, if the measurement falls within the tail area it is declared representative of a detected abnormal event or condition. Optionally, at 1214, at least one of an alert, therapy and the like are provided in response to the detected abnormal event or condition. If the measurement does not fall within the tail area, process flow returns to 1202. In one example, if the measurement of the first physiological parameter is a non-event, it may then be included in a subsequent computation of the first distribution of measurements at 1202.

Several variations of the method 1200 are possible. In certain examples, the physiological parameter is selected from the group consisting essentially of heart sounds, heart timing intervals and heart depolarization or other amplitudes. Instead of using patient-based or population-based data for computing the first distribution, certain examples could use a mathematically-described distribution function, or fitting of actual patient or population based measurements of the first physiological parameter to at least one specified distribution, such as a mathematical function, of a family of specified distributions. The first distribution may be updated on an ongoing basis, and corrupted, confounded, invalid, or event-related measurements can be excluded from the original computation of the first distribution, or such ongoing re-computation.

Figure 13:
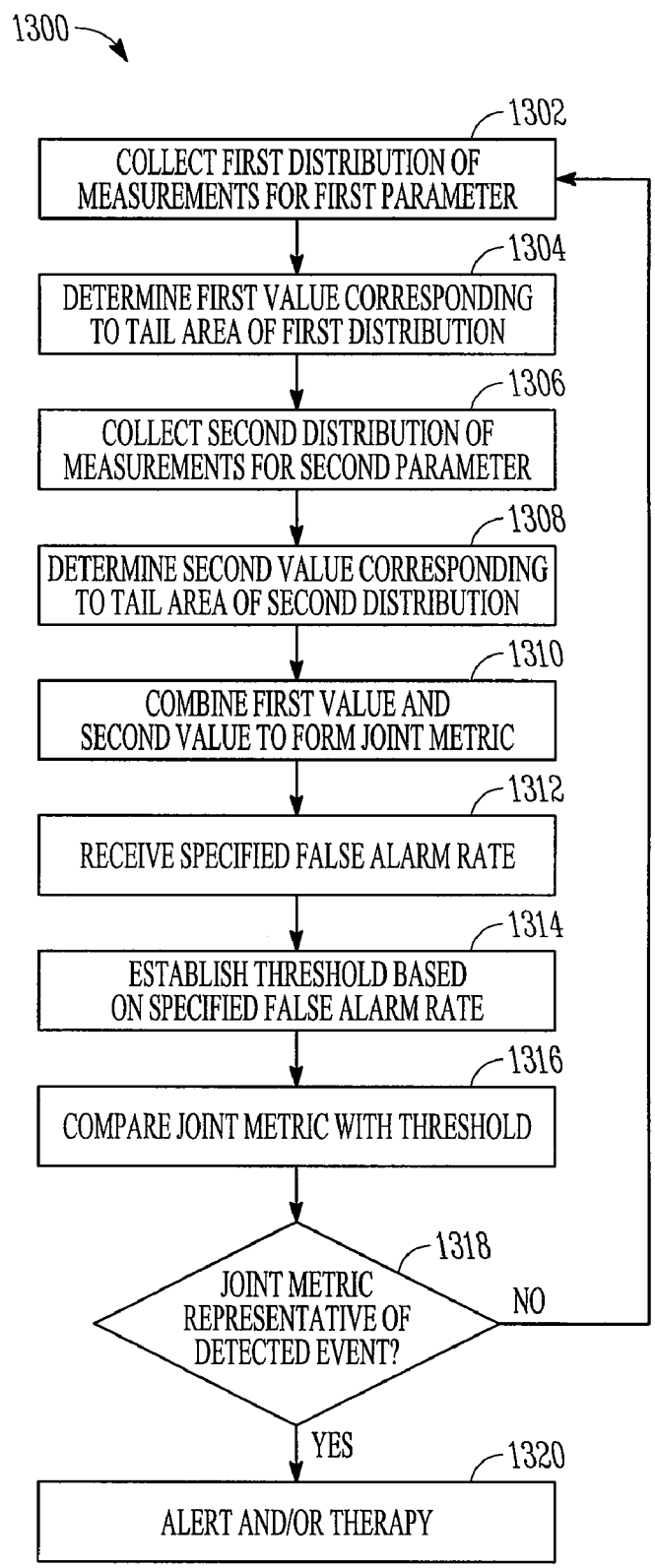
FIG. 13 is a block diagram showing one example of a Constant False Alarm Rate (CFAR) method for event detection using a multiple non-event probability distribution functions.

FIG. 13 is an example of a flow chart illustrating yet another example of an event detection method 1300. In the example of FIG. 13, at 1302, a first distribution of measurements is collected for a first physiological parameter. At 1304, a first value is determined that corresponds to a tail area of the first distribution from a first physiological parameter measurement toward an end point of the first distribution. At 1306, a second distribution of measurements for a different second physiological parameter is collected. At 1308, a second value is determined corresponding to a tail area of the second distribution from a second physiological parameter measurement toward an end point of the second distribution. At 1310 the first value is combined with the second value to form a joint metric. At 1312, a specified false alarm rate is input, for instance by a clinician. In one example, the false alarm rate is input by a clinician through, but not limited to, a keyboard, keypad, touch screen, receiver and the like. At 1314 a specified threshold is established based on the predetermined false alarm rate (FAR). In one example, the FAR is set in an implantable or external device by the clinician according to a desired acceptable false alarm rate, specificity, or sensitivity. The FAR is set by the clinician without having to know detailed information regarding a threshold value for a physiological parameter. Further, the FAR is input by the clinician and used in this method independent of any statistics for a distribution of a physiological parameter. At 1316, the joint metric is compared with the specified threshold. At 1318, in one example, if the joint metric exceeds the specified threshold, the measurements are considered representative of a detected abnormal event. Otherwise, the process flow returns to 1302. In another option, if the joint metric is less than the predetermined threshold the measurements are considered representative of a detected event or condition. Otherwise, the process flow returns to 1302. At 1320, if the joint metric is representative of a detected abnormal event or condition, then at least one of an alert, therapy, or the like are provided in response. In another example, where the measurements of the first physiological parameter and the second physiological parameter are deemed to be non-event measurements, they can be included in the first distribution and second distribution respectively, if desired.

Several variations of the method are possible. In one example, event-related measurements are excluded from computing the first and second distributions of cardiac or other correlated or uncorrelated physiological parameters. In certain examples, determining the first and second values includes determining first and second probabilities of false alarm for the physiological parameter measurements of the first and second physiological parameters. The method 1300 includes, in yet another option, associating the first physiological parameter measurement with the second physiological parameter measurement. Optionally, associating the first and second physiological parameter measurements includes associating the most recent first and second physiological parameter measurements. The method 1300 includes, in yet another example, attenuating at least one of the first and second tail values (e.g., setting the values to negligible amounts) if at least one of a first sensor for the first physiological parameter and a second sensor for the second physiological parameter is corrupted, confounded, event-related, or otherwise deemed invalid.

Figure 14:
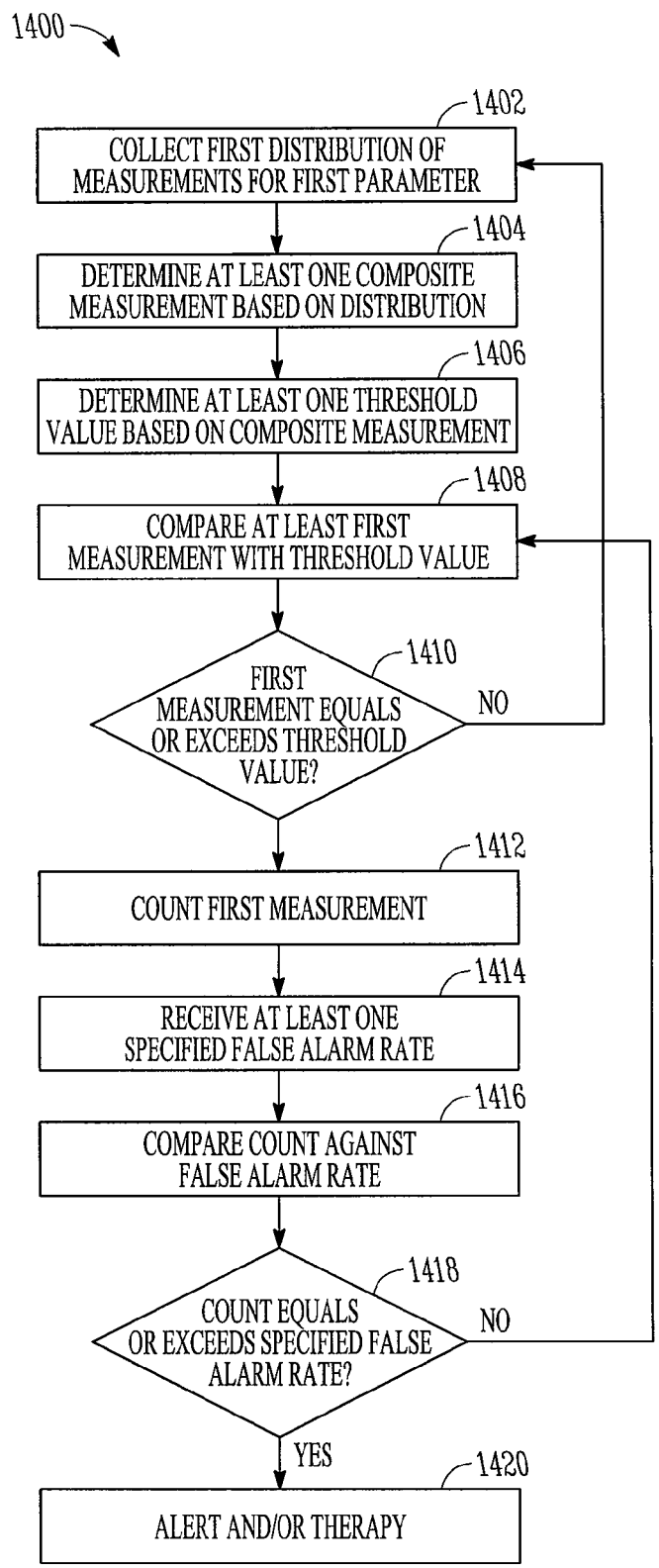
FIG. 14 is a block diagram showing yet another example of a Constant False Alarm Rate (CFAR) method for event detection using a non-event probability distribution function.

FIG. 14 is an example of a flow chart showing still another event detection method 1400. At 1402 a first distribution of measurements is collected for a first physiological parameter. At 1404, at least one composite measurement is determined based on the distribution, for instance, using one or more mean, median, percentile values, or the like. At 1406, at least one threshold value based on the composite measurement is determined. At 1408, a first measurement is compared with the threshold value. At 1410, if the first measurement equals or exceeds the threshold value, the value is counted at 1412. Otherwise, the process flow returns to 1402. At 1414, a specified false alarm rate is received. In one example, the false alarm rate is input by a clinician through, but not limited to, a keyboard, keypad, touch screen, receiver and the like. At 1416, the count is compared against at least one predetermined false alarm rate (FAR). In certain examples, the FAR is set by the clinician according to a desired false alarm rate, specificity, sensitivity, or the like in an implantable medical device or an external system, such as a local external programmer or an external remote server. At 1418, if the count equals or exceeds the FAR, then the count is considered representative of a detected abnormal event or condition. Otherwise, the process flow returns to 1408. At 1420, at least one of a responsive alert, therapy, or the like are provided.

Several variations for the method 1400 are possible. In certain examples, determining the at least one composite measurement includes weighting more heavily the most recent measurements of the first distribution of measurements. In certain examples, weighting the most recent measurements of the first distribution of measurements includes counting the most recent measurements multiple times in the first distribution of measurements. Determining the at least one threshold value may include scaling or otherwise modifying the composite measurement by a constant. In certain examples, the composite measurement is multiplied by the constant.

Determining the at least one threshold value may include modifying the composite measurement by a first constant and a second constant, or determining and using multiple threshold values or multiple specified false alarm rates.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A method comprising:
   determining a first distribution of values for a first physiological parameter, the first distribution of values determined using physiological data collected by a physiological sensor of an implantable medical device;

determining one or more values corresponding to at least a first tail area of the first distribution, the first tail area extending from at least one measurement of the first physiological parameter toward an end point of the distribution;

receiving a specified false alarm rate;

establishing a threshold based on the specified false alarm rate and the first distribution of values, the threshold value changing according to a change in the first distribution of values;

comparing the one or more values to the threshold; and determining that the measurement is representative of a detected event using the comparison.

2. The method of claim 1, wherein determining the first distribution of values for the first physiological parameter includes using only non-event measurements of the first physiological parameter.

3. The method of claim 1, wherein determining the first distribution of values includes using a first distribution of measurements for a first cardiac parameter.

4. The method of claim 1, wherein determining one or more values corresponding to at least the first tail area of the first distribution includes determining a first probability of false alarm for the measurement of the first physiological parameter.

5. The method of claim 1, wherein receiving the specified false alarm rate includes inputting the specified false alarm rate independent of at least the first distribution of values for the first physiological parameter.

6. The method of claim 1, further comprising updating the first distribution of values for the first physiological parameter by collecting additional non-event values of the first physiological parameter.

7. The method of claim 6, wherein updating the first distribution of values for the first physiological parameter includes excluding at least one of corrupted, confounded, or event-related measurements.

8. The method of claim 1, further comprising transforming the one or more values corresponding to at least the first tail area of the first distribution into one or more transformed values with observable significance with respect to at least one of other transformed values and the threshold.

9. The method of claim 1, further comprising:
determining a first value corresponding to the first tail area of the first distribution, the first tail area extending from a first measurement of the first physiological parameter toward an end point of the distribution;
determining a second value corresponding to a second tail area of the first distribution, the second tail area extending from a second measurement of the first physiological parameter toward an end point of the distribution;
combining the first value with the second value to form a joint metric; and
comparing the one or more values to the threshold includes comparing the joint metric to the threshold.

10. A method comprising:
using a first distribution representative of measurements for a first physiological parameter, the first distribution collected by a physiological sensor of an implantable medical device;
receiving a specified false alarm rate;
computing an event detection threshold value based on the specified false alarm rate and the first distribution, the threshold value changing according to a change in the first distribution of values, and the event detection threshold value corresponds to a first tail area of the first distribution extending from the event detection threshold value toward an end point of the first distribution;
obtaining a measurement of the first physiological parameter with the implantable medical device;
comparing the measurement of the first physiological parameter to the event detection threshold value; and
declaring the measurement as representative of a detected event if the measurement falls within the tail area.

11. The method of claim 10, wherein using the first distribution includes using only non-event measurements of the first physiological parameter.

12. The method of claim 11, further comprising:
updating the first distribution of measurements for the first physiological parameter; and
excluding from the updating at least one of corrupted, confounded, or event-related measurements.

13. A method comprising:
determining a first distribution of measurements for a first physiological parameter, the first distribution of measurements determined using physiological data collected by a physiological sensor of an implantable medical device;
determining a first value corresponding to a first tail area of the first distribution, the first tail area extending from a first physiological parameter measurement toward an end point of the first distribution;
determining a second distribution of measurements for a second physiological parameter, the second distribution of measurements determined by the implantable medical device, and the second physiological parameter is different from the first physiological parameter;
determining a second value corresponding to a second tail area of the second distribution, the second tail area extending from a second physiological parameter measurement toward an end point of the second distribution;
combining the first value with the second value to form a joint metric where the first value and second values are based on their respectively different first and second physiological parameters;
receiving a specified false alarm rate;
establishing a shared common threshold based on a specified false alarm rate;
comparing the joint metric including the combined first and second values with the shared common threshold; and
determining that the first and second physiological parameter measurements are representative of a detected event using the comparison.

14. The method of claim 13, wherein determining the first and second values includes determining first and second probabilities of false alarm for the physiological parameter measurements of the first and second physiological parameters.

15. A method comprising:
determining a first distribution of measurements for a first physiological parameter, the first distribution of measurements determined using physiological data collected by a physiological sensor of an implantable medical device;
determining at least one composite measurement based on the distribution;
determining at least one threshold value based on the composite measurement;
comparing at least a first measurement with the threshold value;

counting the first measurement if the measurement equals or exceeds the threshold value;

receiving at least one specified false alarm rate;

comparing the count against the at least one specified false alarm rate; and determining whether the count is representative of a detected event using the comparison.

16. The method of claim 15, wherein determining the at least one threshold value based on the composite measurement includes determining a first threshold value and a second threshold value.

17. The method of claim 16, wherein counting the first measurement includes counting the first measurement in a first count if the measurement equals or exceeds the first threshold value, and counting the first measurement in a second count if the measurement equals or exceeds the second threshold value.

18. The method of claim 17, wherein comparing the count against the at least one specified false alarm rate includes comparing the first count against a first specified false alarm rate and comparing the second count against a second specified false alarm rate.

19. The method of claim 15, wherein receiving the at least one specified false alarm rate includes inputting the at least one specified false alarm rate independent of the first distribution of measurements for the first physiological parameter.

20. An apparatus comprising:
an implantable medical device comprising:
a physiological sensor to collect at least a first distribution of measurements for a first physiological parameter; and
a processor circuit comprising:
a value determination module to determine one or more values corresponding to at least a first tail area of the first distribution of the first physiological parameter toward an end point of the distribution,
a comparator to compare the one or more values with a threshold, the threshold based on a specified false alarm rate and the first distribution of measurements, the threshold value changing according to a change in the first distribution of measurements, and
an event indicator to provide an event indication if the one or more values is representative of a detected event using the comparison.

21. The apparatus of claim 20, wherein the implantable medical device includes a pulse generator.

22. The apparatus of claim 20, wherein the physiological sensor is adapted to collect at least the first distribution of measurements for the first physiological parameter selected from the group consisting essentially of heart sound and thoracic impedance.

23. The apparatus of claim 20, wherein the physiological sensor is adapted to collect only non-event measurements of the first physiological parameter.

24. The apparatus of claim 20, wherein the value determination module is adapted to determine a first probability of false alarm for the measurement of the first physiological parameter.

25. The apparatus of claim 24, wherein the value determination module is adapted to determine a heart failure condition confidence for the measurement of the first physiological parameter.

26. The apparatus of claim 20, further comprising a joint metric module adapted to combine a plurality of values into a joint metric.

27. The apparatus of claim 20, further comprising a therapy circuit in communication with the event indicator, wherein the therapy circuit is adapted to control therapy delivered by the implantable medical device in response to the event indicator.

28. The apparatus of claim 20, wherein the implantable medical device includes the processor circuit.

29. The apparatus of claim 20, further comprising an input module adapted to receive the specified false alarm rate independent of the first distribution of measurements for the first physiological parameter.

* * * * *